Figure 1A:
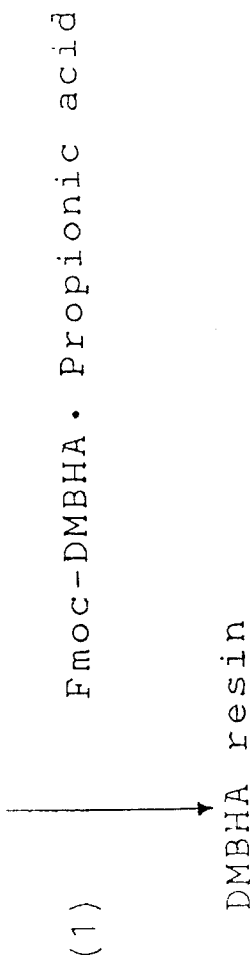

United States Patent [19]

Fujii et al.

[11] Patent Number: 5,571,892

[45] Date of Patent: Nov. 5, 1996

[54] POLYPEPTIDE AND ANTI-HIV DRUG PREPARED THEREFROM

[75] Inventors: Nobutaka Fujii, Hirakata; Naoki Yamamoto, Tokyo, both of Japan

[73] Assignee: Seikagaku Kogyo Co., Ltd., Tokyo, Japan

[21] Appl. No.: 856,026

[22] PCT Filed: Sep. 10, 1991

[86] PCT No.: PCT/JP91/01201

§ 371 Date: Jul. 1, 1992

§ 102(e) Date: Jul. 1, 1992

[87] PCT Pub. No.: WO92/04374

PCT Pub. Date: Mar. 19, 1992

[30] Foreign Application Priority Data

Sep. 11, 1990 [JP] Japan .................................. 2-238922

[51] Int. Cl.⁶ .............................. A61K 38/10; C07K 7/08
[52] U.S. Cl. ........................................................... 530/326
[58] Field of Search ............................. 530/326; 514/13

[56] References Cited

U.S. PATENT DOCUMENTS 5,449,752  9/1995  Fujii et al. ............................... 530/326

FOREIGN PATENT DOCUMENTS

| 2-500194 | 1/1990 | Japan . |
| 2-53799 | 2/1990 | Japan . |
| 2-152987 | 6/1990 | Japan . |
| 2-167230 | 6/1990 | Japan . |

OTHER PUBLICATIONS

Leff, Bioworld Today, (Oct. 28, 1994) vol. 5, No. 210 p. 1.
Saag et al., J. of Acquired Immune Def. Synd., vol. 7 Suppl. 2, S2–S11, (1994).
Hammer et al., J. of Acquired Immune Def. Synd., vol. 7 Suppl. 2, (1994) pp. 524–537.
Richman et al., J. of Virology, Mar. 1994, pp. 1660–1666. vol. 68 No. 3.
ASM News vol. 56 No. 7 Jul. 1990 (American Society for Microbiology).
Masuda et al. Biochem. and Biophys. Res. Commun. vol. 189 No. 2 (1992) pp. 845–850.
T. Mula et al. "Primary Structures and Functions of Anti-–Lipopolysaccharide Factor and Tachyplesin Peptide Found in Horseshoe Crab Hemocytes," *Advances in Experimental Medicine and Biology*, vol. 256, 1990, 273–285, New York.
Nakamura et al., "Tachyplesin, a class of Antimicrobial Peptide from the Hemocytes of the Horseshoe Crab (Tachypleus tridentatus)". J. Biol. Chem. vol. 263, No. 32, Nov. 15, pp. 16709–16713, (1988).
Akaji et al., "Studies on Peptides. CLXVIII. Syntheses of Three Peptides Isolated from Horseshoe Crab Hemocytes, Tachyplesin I, Tachyplesin II, and Polyphemusin I". Chem. Pharm. Bull. 37 2661–2664 (1989).
Miyata et al., "Antimicrobial Peptides, Isolated from Horseshoe Crab Hemocytes, Tachyplesin II, and Polyphemusins I and II: Chemical Structures and Biological Activity". J. Biochem. 106, 663–668 (1989).
Taisha "LPS–binding protein and peptide, esp. chem. structures and biol. activities thereof". Metabolism, vol. 26, No. 5 429–439 (1989).

*Primary Examiner*—Jeffrey E. Russel
*Attorney, Agent, or Firm*—Pennie & Edmonds

[57] ABSTRACT

A novel polypeptide represented by the following formula (I) (SEQ. ID NO: 1)

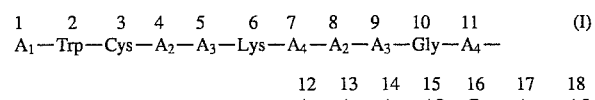

or a salt thereof, and an anti-HIV agent containing the same as an effective ingredient. According to this invention, there can be provided a novel polypeptide having an antiviral activity against human immunodeficiency virus (HIV), a pharmaceutically acceptable salt thereof, and an anti-HIV agent containing the same as an effective ingredient.

15 Claims, 2 Drawing Sheets

(1) Aminomethyl resin →  Fmoc-DMBHA · Propionic acid  → DMBHA resin

Condensation of protected amino acids in the order of the peptide sequence →

(2) Fmoc-¹⁷Arg(Mtr)-DMBHA resin →

(3) Fmoc-¹⁶Cys(MBzl)-¹⁷Arg(Mtr)DMBHA resin →

(4) Resin wherein the protected amino acids at the 15- to 1-positions are condensed

POLYPEPTIDE AND ANTI-HIV DRUG PREPARED THEREFROM

TECHNICAL FIELD

This invention relates to a novel polypeptide or a salt thereof. More detailedly, this invention relates to a novel polypeptide exhibiting a strong affinity to lipopolysaccharides, particularly endotoxins and having an improved antibacterial activity and an improved antiviral activity, a pharmaceutically acceptable salt thereof, and an anti-HIV agent containing the same as an effective ingredient.

BACKGROUND ART

Heretofore, as shown in the following literatures, there have been reported by Nakamura, Iwanaga, Niwa, et al. polypeptides (Tachyplesin and Polyphemusin) exhibiting an affinity to endotoxins and being derived from horseshoe crabs and their pharmacological properties.

(i) J. Biol. Chem., 263, 16709–16713 (1988)

(ii) Published Searched Application 500194/1990

(iii) Chem. Pharm. Bull., 37, 2661–2664 (1989)

(iv) Japanese Laid-Open Patent Publication No. 53799/1990

(v) Japanese Laid-Open Patent Publication No. 152987/1990

(vi) Japanese Laid-Open Patent Publication No. 167230/1990

(vii) J. Blochem., 106, 663–668 (1989)

(viii) Taisha (Metabolism), 26, 301–311 (1989)

As for polypeptides having an affinity to endotoxins isolated from horseshoe crabs (the genus Tachypleus, the genus Lumulus and the genus Carcinoscorpius), 5 structural analogs exist, to the best of researcher's knowledge, and each of them is a polypeptide having a cyclic structure comprising 17 or 18 natural amino acids. Further, these polypeptides mutually exhibit extremely analogous properties, and such a polypeptide is very interesting as one of key substances whereby horseshoe crabs have been able to be adapted to changes of their external environment and preserve their species from ancient times to the present time as a living fossil.

On the other hand, with respect to maintenance of the existence of human beings who have highly differentiated, drugs are being desired which are expected to have a prophylactic or therapeutic effect on an acquired immune deficiency syndrome (AIDS) caused by infection with a human immunodeficiency virus.

The present inventors paid their attention to the above endotoxin-affinitive polypeptides conjectured to have relation to the strong preservability of species on horseshoe crabs, and made a study of a correlation between structural changes on these substances and the anti-human immunodeficiency virus (HIV) activity. As a result, they found novel polypeptides basically different from the common structure of the known endotoxin-affinitive polypeptides of horseshoe crabs, and, to their surprise, it was ascertained that these novel polypeptides have an excellent effect that their anti-HIV activity values are 10 times or more as large as that of a known endotoxin-affinitive polypeptide.

DISCLOSURE OF INVENTION

This invention was reached based on such a finding and relates to a novel polypeptide represented by the following formula (I) (SEQ. ID. NO: 1)

$$\begin{array}{cccccccccccc}1 & 2 & 3 & 4 & 5 & 6 & 7 & 8 & 9 & 10 & 11 & \text{(I)}\\ A_1-\text{Trp}-\text{Cys}-A_2-A_3-\text{Lys}-A_4-A_2-A_3-\text{Gly}-A_4-\end{array}$$

$$\begin{array}{ccccccc}12 & 13 & 14 & 15 & 16 & 17 & 18\\ A_4-A_2-A_3-A3-\text{Cys}-\text{Arg}-A5\end{array}$$

[wherein $A_1$ denotes a hydrogen atom or one or two amino acid residues of amino acids selected from lysine and arginine, $A_2$ independently denotes a tyrosine, phenylalanine or tryptophan residue, $A_3$ independently denotes an arginine or lysine residue, $A_4$ independently denotes an alanine, valine, leucine, isoleucine, serine, cysteine or methionine residue, $A_5$ denots —OH (derived from the carboxyl group) or —NH$_2$ (derived from the acid-amide group), Cys denotes a cysteine residue, Gly denotes a glycine residue, Lys denotes a lysine residue, Arg denotes an arginine residue, and Trp denotes a tryptophan residue; and the cysteine residues at the 3- and 16-positions may be linked through a disulfide linkage (—S—S—), and when the 7- and 12-positions are both cysteine residues, these may be linked through a disulfide linkage (—S—S—)] or a salt thereof.

The novel polypeptide of the invention has a basically important characteristic that although, in the known polypeptides derived from the horseshoe crabs, the amino acid residue at the 6-position is a valine (Val) residue in common, its 6-position is a lysine (Lys) residue, a basic amino acid residue having an utterly different property from that of the valine residue.

The novel polypeptide or salt thereof of the invention is described in more detail below.

The novel polypeptide of the invention can be prepared by a method known per se, for example a solid phase synthetic method. Namely, a straight-chain polypeptide of the invention having the above formula (I) can be obtained by linking the carboxyl group of a N-protected arginine to an insoluble resin having amino groups directly or in some case through a spacer having a functional group capable of linking to a carboxyl group and a carboxyl group, successively linking, according to the solid phase synthetic method, the respective protected amino acids of the 16-position to the 1-position of the amino acid sequence represented by the following formula (I) (SEQ. ID NO: 1)

$$\begin{array}{cccccccccccc}1 & 2 & 3 & 4 & 5 & 6 & 7 & 8 & 9 & 10 & 11 & \text{(I)}\\ A_1-\text{Trp}-\text{Cys}-A_2-A_3-\text{Lys}-A_4-A_2-A_3-\text{Gly}-A_4-\end{array}$$

$$\begin{array}{ccccccc}12 & 13 & 14 & 15 & 16 & 17 & 18\\ A_4-A_2-A_3-A3-\text{Cys}-\text{Arg}-A5\end{array}$$

[wherein $A_1$, $A_2$, $A_3$, $A_4$, Cys, Gly, Lys, Arg and Trp are as defined in the above formula (I)], and then eliminating (removing) the insoluble resin and the protecting groups of the amino acids. In this instance, the carboxyl terminus of the amino acid residue at the 17-position can be either free ($A_5$ corresponds to —OH) or converted to an acid amide ($A_5$ corresponds to —NH$_2$). Further in the obtained polypeptide, the two cysteines at the 3- and 16-positions can form a disulfide linkage (—S—S—) through the mercapto groups.

Further, when the 7-position and 12-position are both cysteine residues, these cysteines can form likewise a disulfide linkage.

As for the formation of these disulfide linkage, both two pairs of the cysteines groups can be converted to a disulfide linkage, for example by air oxidation, or either disulfide linkage can be formed according to the method of Atherton, E., et al.; J. Chem. Soc., Perkin Trans. 1, 1985, 2065, namely through steps of previously selectively protecting the mercapto groups of either pair of cysteines at the 3- and 16-positions and the 7- and 12-positions with a protecting group, t-BuS (t-butylthio) and the mercapto groups of the other pair of cysteines with a protecting group, Acm (acetamidomethyl); deprotecting the t-BuS, partially oxidizing the mercapto groups; and then deprotecting the Acm according to a known method.

Respective amino acids to be used in the solid phase synthetic method can be commonly L-forms or commonly D-forms.

As for the insoluble resins having amino group to be used in synthesizing the novel polypeptide of the invention, any of such resins can be used so long as it can link through its amino groups to the carboxyl group of the N-protected arginine at the C-terminus or in some case to the carboxyl group of the spacer linked thereto and thereafter can be eliminated (removed).

Examples of such an insoluble resin are aminomethyl resins (aminomethylated styrene-divinylbenzene copolymers), benzhydrylamine resins, methylbenzhydrylamine resins and aminomethylphenoxymethyl resins and their derivatives, etc. When a benzhydrylamine resin, methylbenzhydrylamine resin, dimethoxybenzhydrylamine (DMBHA) resin or aminomethylphenoxymethyl resin is used, an amide is directly obtained by cleavage, but an aminomethyl resin is preferred in view of yield.

As the spacer having a functional group capable of linking to the carboxyl group and a carboxyl group, there can, for example, be mentioned one capable of converting the carboxyl group of arginine to a p-carboxymethylbenzyl ester, but there is no particular limitation on the spacer.

The protected amino acid is an amino acid whose functional groups are protected with protecting group by known method, and various protected amino acids are sold on the market.

In synthesizing the polypeptide of the invention, it is preferred to choose any one of the following protecting groups. A protecting group for the α-amino group of an amino acid is Boc (t-butyloxycarbonyl) or Fmoc (9-fluorenylmethyloxycarbonyl). A protecting group for the guanidino group of arginine (Arg) is Tos (tosyl), $NO_2$ (nitro), Mtr (4-methoxy-2,3,6-trimethylbenzenesulfonyl) or Pmc (2,2,5,7,8-pentamethylchroman-6-sulfonyl). As a protecting group for the mercapto group of cysteine (Cys) is mentioned Bzl (benzyl), MBzl (4-methoxybenzyl), 4-MeBzl (4-methylbenzyl), Acm (acetamidomethyl), Trt (trityl), Npys (3-nitro-2-pyridinesulfenyl), t-Bu(t-butyl) or t-BuS (t-butylthio), and MBzl, 4-MeBzl, Trt, Acm and Npys are preferred. A protecting group for the hydroxyl group of tyrosine (Tyr) is Bzl, $Cl_2Bzl$ (2,6-dichlorobenzyl) or t-Bu, but the group may be not protected. A protecting group for the ε-amino group of lysine (Lys) is Z (benzyloxycarbonyl), ClZ (2-chlorobenzyloxycarbonyl), Boc or Npys. It is preferred to select as each protecting group a proper one from ones known per se in accordance with synthetic conditions for the peptide.

The coupling of protected amino acids can be carried out according to a usual condensation method such as, for example, a DCC (dicyclohexylcarbodiimide) method, DIPCDI (diisopropylcarbodiimide) method [Tartar, A. et al.; J. Org. Chem., 44 5000 (1979)], active ester method, mixed or symmetrical acid anhydride method, carbonyldiimidazole method, DCC-HOBt (1-hydroxybenzotriazole) method [K önig W. et al.; Chem. Ber., 103, 788, 2024, 2034, (1970)] or diphenylphosphoryl azide method, but preferred are the DCC method, DCC-HOBt method, DIPCDI-HOBt method and symmetrical acid anhydride method. These condensation reaction is, usually, carried out in an organic solvent such as dichloromethane or dimethylformamide or a mixed solvent thereof. As a deblocking reagent for the protecting group for an α-amino group is used trifluoroacetic acid/dichloromethane, HCl/dioxane, piperidine/dimethylformamide or the like, and appropriate selection is made according to the kind of the protecting group. Further, the degree of the progress of condensation reaction in each step of synthesis is pursued by the method of E. Kaiser et al. [Anal. Biochem., 34, 595 (1970)] (the ninhydrin reaction method).

According to the foregoing ways, there can be obtained a protected peptide resin having a desired amino acid sequence.

When an aminomethyl resin derivative was used as the insoluble resin, the resin can be removed, for example, by treating the protected peptide resin with ammonia in an appropriate solvent. The resulting protected peptide is then treated with hydrogen fluoride to obtain a polypeptide amide represented by the above formula and freed of all the protecting groups. When a benzhydrylamine resin, methylbenzhydrylamine resin, aminomethylphenoxymethyl resin or DMBHA resin [Funakoshi, S. et al.; J. Chem. Soc., Chem, Commun., 1988, 382] was used as the insoluble resin, the resin and the protecting groups can simultaneously be removed by treating the protected peptide resin with hydrogen fluoride, TFMSA (trifluoromethanesulfonic acid) [published by Academic Press, edited by E. Gross; Yajima, H. et al.; "The Peptides" vol. 5, page 65 (1983)], TMSOTf (trimethylsilyl triflate) [Fujii, N. et al.; J. Chem. Soc., Chem. Commun., 1987, 274] or TMSBr (trimethylsilyl bromide) [Fujii, N. et al.; Chem. Pharm. Bull., 35, 3880 (1987)] or the like.

Then, if desired, the resulting polypeptide is reduced with 2-mercaptoethanol, DTT (dithiothreitol) or the like to surely make the mercapto groups of the cysteines reduced form, and then oxidized to obtain a cyclic polypeptide belonging to the invention.

The oxidation treatment can be carried out by a known method. Usually, such oxidizing agent as oxygen in the air or a ferricyanate (e.g. potassium ferricyanide) is used.

The thus obtained polypeptide can be isolated and purified by means known per se for polypeptides, for example, extraction, recrystallization, various chromatographies (gel filtration, ion exchange, partition, adsorption, reverse-phase), electrophoresis, counter-current distribution, etc., and reverse-phase high performance liquid chromatography is the most effective.

As specific examples of polypeptides of the invention represented by the formula (I), there can be mentioned those of the following formulae (1) to (22) (SEQ. ID NOS: 2 to 23 respectively). In the following formulae (1) to (22), each symbol denotes the corresponding amino acid residue by the internationally admitted three-letter expression. Namely each symbol denotes the residue of the following amino acids.

| Arg: | Arginine | Trp: | Tryptophan |
| Cys: | Cysteine | Tyr: | Tyrosine |
| Lys: | Lysine | Gly: | Glycine |
| Phe: | Phenylalanine | Ile: | Isoleucine |
| Ser: | Serine | Leu: | Leucine |
| Met: | Methionine | Val: | Valine |
| Ala: | Alanine | | |

|     | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| (1) (SEQ. ID NO:2) | | | Trp | Cys | Tyr | Arg | Lys | Cys | Tyr | Arg | Gly | Ile | Cys | Tyr | Arg | Lys | Cys | Arg-NH₂ |
| (2) (SEQ. ID NO:3) | | Arg | Trp | Cys | Tyr | Arg | Lys | Cys | Tyr | Arg | Gly | Ile | Cys | Tyr | Arg | Lys | Cys | Arg-NH₂ |
| (3) (SEQ. ID NO:4) | Arg | Arg | Trp | Cys | Tyr | Arg | Lys | Cys | Tyr | Arg | Gly | Ile | Cys | Tyr | Arg | Lys | Cys | Arg-NH₂ |
| (4) (SEQ. ID NO:5) | | Arg | Trp | Cys | Tyr | Arg | Lys | Cys | Tyr | Arg | Gly | Met | Cys | Tyr | Arg | Lys | Cys | Arg-NH₂ |
| (5) (SEQ. ID NO:6) | Arg | Arg | Trp | Cys | Tyr | Arg | Lys | Cys | Tyr | Arg | Gly | Leu | Cys | Tyr | Arg | Lys | Cys | Arg-NH₂ |
| (6) (SEQ. ID NO:7) | | | Trp | Cys | Tyr | Arg | Lys | Cys | Tyr | Arg | Gly | Ile | Cys | Tyr | Arg | Lys | Cys | Arg-NH₂ |
| (7) (SEQ. ID NO:8) | | Arg | Trp | Cys | Tyr | Arg | Lys | Cys | Tyr | Arg | Gly | Ile | Cys | Tyr | Arg | Lys | Cys | Arg-NH₂ |
| (8) (SEQ. ID NO:9) | Arg | Arg | Trp | Cys | Tyr | Arg | Lys | Cys | Tyr | Arg | Gly | Ile | Cys | Tyr | Arg | Lys | Cys | Arg-NH₂ |
| (9) (SEQ. ID NO:10) | | Arg | Trp | Cys | Tyr | Arg | Lys | Cys | Tyr | Arg | Gly | Leu | Cys | Tyr | Arg | Lys | Cys | Arg-NH₂ |
| (10) (SEQ. ID NO:11) | Arg | Arg | Trp | Cys | Tyr | Arg | Lys | Cys | Tyr | Arg | Gly | Val | Cys | Tyr | Arg | Lys | Cys | Arg-NH₂ |
| (11) (SEQ. ID NO:12) | | | Arg | Trp | Cys | Tyr | Arg | Lys | Cys | Tyr | Arg | Gly | Ile | Cys | Tyr | Arg | Lys | Cys-Arg-NH₂ |
| (12) (SEQ. ID NO:13) | | Arg | Trp | Cys | Tyr | Arg | Lys | Cys | Tyr | Arg | Gly | Ile | Cys | Tyr | Arg | Lys | Cys | Arg-NH₂ |
| (13) (SEQ. ID NO:14) | Arg | Arg | Trp | Cys | Tyr | Arg | Lys | Cys | Tyr | Arg | Gly | Ile | Cys | Tyr | Arg | Lys | Cys | Arg-NH₂ |
| (14) (SEQ. ID NO:15) | | Arg | Trp | Cys | Tyr | Arg | Lys | Cys | Tyr | Arg | Gly | Ser | Cys | Tyr | Arg | Lys | Cys | Arg-NH₂ |
| (15) (SEQ. ID NO:16) | Arg | Arg | Trp | Cys | Tyr | Arg | Lys | Cys | Tyr | Arg | Gly | Ala | Cys | Tyr | Arg | Lys | Cys | Arg-NH₂ |
| (16) (SEQ. ID NO:17) | | Arg | Trp | Cys | Trp | Arg | Lys | Cys | Trp | Lys | Gly | Leu | Cys | Tyr | Arg | Lys | Cys | Arg-NH₂ |
| (17) (SEQ. ID NO:18) | Arg | Arg | Trp | Cys | Trp | Arg | Lys | Cys | Trp | Lys | Gly | Leu | Cys | Tyr | Arg | Lys | Cys | Arg-NH₂ |
| (18) (SEQ. ID NO:19) | | Arg | Trp | Cys | Phe | Lys | Lys | Cys | Phe | Lys | Gly | Ser | Cys | Phe | Lys | Lys | Cys | Arg-NH₂ |
| (19) (SEQ. ID NO:20) | Arg | Arg | Trp | Cys | Phe | Lys | Lys | Cys | Phe | Lys | Gly | Ser | Cys | Tyr | Lys | Lys | Cys | Arg-NH₂ |
| (20) (SEQ. ID NO:21) | | Arg | Trp | Cys | Tyr | Arg | Lys | Ala | Tyr | Lys | Gly | Leu | Ala | Tyr | Arg | Lys | Cys | Arg-NH₂ |
| (21) (SEQ. ID NO:22) | | Arg | Trp | Cys | Tyr | Arg | Lys | Ala | Tyr | Lys | Gly | Val | Tyr | Arg | Lys | Cys | | Arg-NH₂ |
| (22) (SEQ. ID NO:23) | Arg | Arg | Trp | Cys | Tyr | Arg | Lys | Cys | Tyr | Lys | Gly | Ile | Ser | Tyr | Arg | Lys | Cys | Arg-NH₂ |

The polypeptides of the invention to be thus obtained and represented by the formula (I) have, likewise in the known polypeptides derived from horseshoe crabs, an ability to bind to endotoxins, an antibacterial activity, an activity to hemolyze endotoxin-sensitized hemocytes and an antiviral activity, and particularly have a good antiviral activity against human immunodeficiency viruses (HIV). Namely, these polypeptides exhibit a ten times or more as high anti-HIV activity as Tachyplesin I, a known polypeptide, exhibits, and some of the polypeptides exhibit several thousand times the anti-HIV activity that Tachyplesin I exhibits.

In the known polypeptides derived from horseshoe crabs, it is revealed, as their structural characteristics, that, due to the existence of 4 Cys residues at the 3-, 7-, 12- and 16-positions, they take a β-sheet structure such that the part at 9- and 10positions is a turning portion by β-turn and the peptide part of the 3-position to 8-position and the peptide part of the 11-position to 16-position face each other, and 4 Cys residues at the 3- and 16-positions and at the 7- and 12-positions link through the respective two disulfide linkages (—S—S—). As structural characteristics for the manifestation of an antiviral activity of the polypeptides whose 6-position is converted to Lys, compounds of the invention, the existence of structural parts whose constitutive amino acid sequences are extremely alike with each other, as is seen in $^3$Cys $^4$A$_2$ $^5$A$_3$ $^6$Lys, facing $^{13}$A$_2$ $^{14}$A$_3$ $^{15}$A$_3$ $^{16}$Cys is basically necessary, and $^2$Trp and $^{17}$Arg are indispensable. It is characterized that further by linking a basic amino acid prescribed in A$_1$ to these structural parts at the 1-position, a structure such that an anti-HIV activity is extremely highly manifested is brought about.

The polypeptide of the invention represented by the formula (I) exhibits a basic property due to the characteristic of the constitutive amino acids, and thus forms a salt by acid addition. For example, the polypeptide forms a salt with an inorganic acid (hydrochloric acid, hydrobromic acid, phosphoric acid, nitric acid, sulfuric acid or the like) or an organic carboxylic acid (acetic acid, propionic acid, maleic acid, succinic acid, malic acid, citric acid, tartaric acid, salicylic acid or the like) or an organic sulfonic acid (methanesulfonic acid, p-toluenesulfonic acid or the like). The polypeptide of the invention represented by the formula (I) can be used as such a pharmaceutically acceptable salt.

The drug of the invention is prepared as a pharmaceutical composition comprising a polypeptide represented by the formula (I) or salt thereof as an effective ingredient, and a pharmacologically acceptable carrier selected in accordance with the administration method and administration form of the drug. Namely, the drug of the invention is orally or parenterally administered in accordance with the object of treatment or disinfect of an in vivo viral disease or the in vitro viral infection part, and can be prepared as a preparation such as powder, granules, a solution for injection or oral aministration, tablets, suppositories, pessaries, ointment, cream or aerosol, using appropriate pharmaceutical carriers in accordance with the administration method.

When the drug of the invention is directly administered as an injection to a living body, the polypeptide or its salt of the invention can continuously or intermittently administered in an amount of 10 to 5,000 mg per kg of human body weight and per one day and by intravenous drip as a solution in physiological saline.

BRIEF DESCRIPTION OF THE FIGURES 1A–B

Figure 1B:
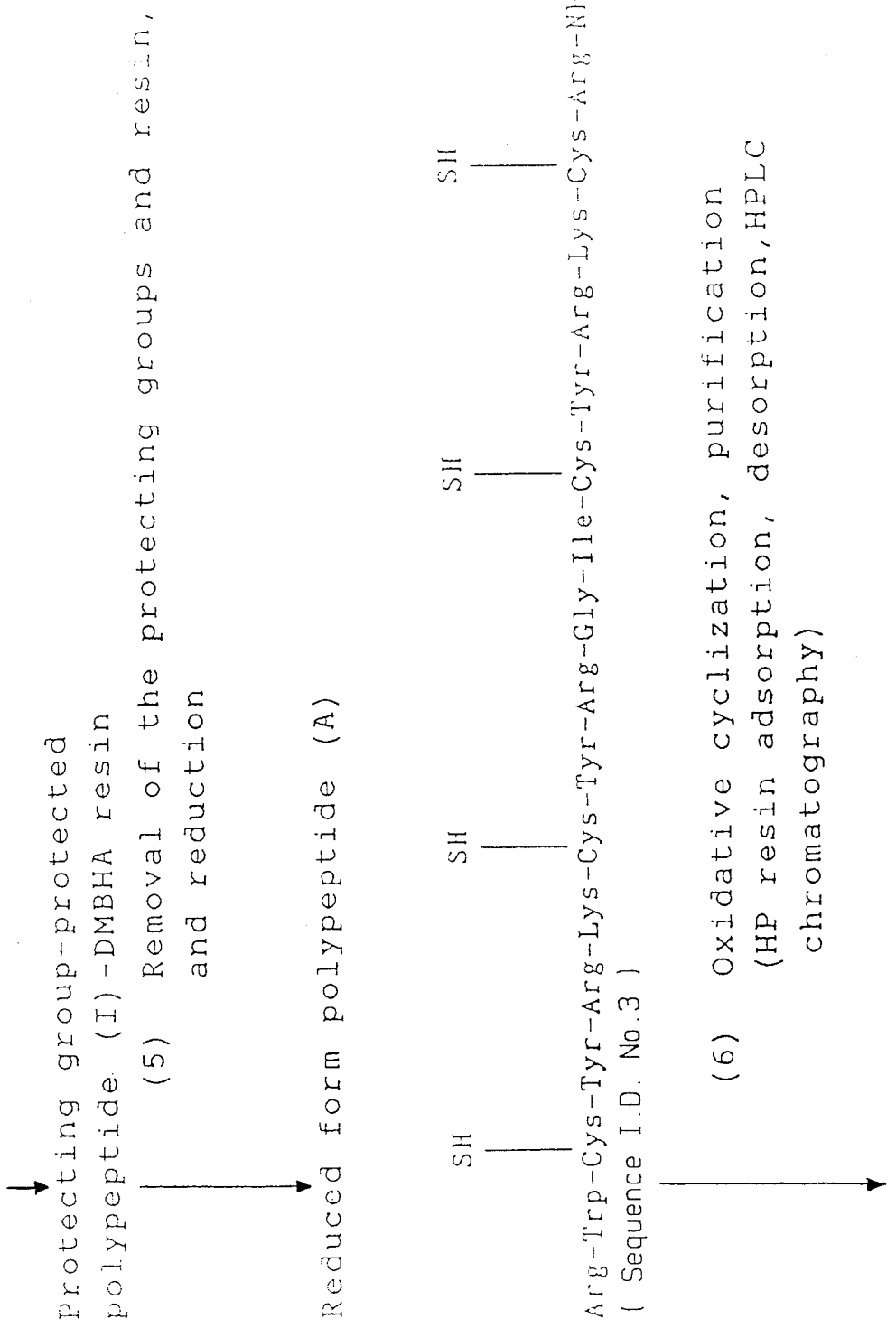

FIGS. 1A–B show an exemplified schematic drawing of steps for synthesizing the novel polypeptide of the invention.

BEST MODE OF CARRYING OUT THE INVENTION

This invention is further specifically described below according to examples, but not limited at all thereby.

Apparatuses and reagents used in the following examples are as follows.

HPLC apparatus: Waters Co. (USA) Model 600

Column of the apparatus:

Asahipak ODP-90

(Asahi Chemical Industry Co., Ltd.)

Fmoc amino acid: produced by Kokusan Kagaku Co., Ltd.

Amino resin and condensing agent: produced by Peptide Kenkyusho Co., Ltd.

FAB-MS (FAB-mass spectrograph):

VG Co. (USA), Model ZAB-SE

EXAMPLE 1

Synthesis of the polypeptide (A) (SEQ. ID NO: 3) of the following formula

```
 1   2   3   4   5   6   7   8   9  10                                    (A)
Arg—Trp—Cys—Tyr—Arg—Lys—Cys—Tyr—Arg—Gly—

11  12  13  14  15  16  17  18
Ile—Cys—Tyr—Arg—Lys—Cys—Arg—NH₂
```

In the above formula (A) (SEQ. ID NO: 3), Arg, Trp, Cys, Tyr, Lys, Gly and Ile denote the aforementioned amino acid residues, and the Cys residues at the 3- and 16-positions and at the 7- and 12-positions are linked respectively through disulfide linkage.

(1) Introduction into an aminomethyl resin of Fmoc-DMBHA-CH₂CH₂COOH
[(3-(α-Fmoc-amino-4-methoxybenzyl)-4-methoxyphenyl) propionic acid]

270 mg (0.2 mmole) of an aminomethyl resin (0.74 meq/g) and 268.5 mg (0.5 mmole, 2.5 eq) of Fmoc-DMB-HACH-CH₂CH₂COOH (MW 537) were placed in a solid phase-synthesizing column, and condensation reaction was carried out for 2 hours by the method of DIPCDI-HOBt in DMF according to the method of Guo, L. et al. [Chem. Pharm. Bull., 36, 4989 (1988)].

After the completion of the condensation reaction, coupling was carried out for the protection of the free amino groups using acetic anhydride (DMBHA resin).

(2) Introduction of arginine of the 17-position into the DMBHA resin

After removing the Fmoc groups of the DMBHA resin prepared in (1) with 20% piperidine/DMF, 2.5 eq of Fmoc-Arg(Mtr)-OH based on the DMBHA resin was added, and condensation reaction was carried out in DMF according to the DIPCDI-HOBt method.

The degree of progress of the condensation reaction was pursued by measurement according to the ninhydrin test of Kaiser, E. et al. [And. Biochem., 34, 595 (1970)].

(3) Introduction of cysteine of the 16-position

After the removal of the Fmoc groups of the DMBHA resin, prepared in (2), into which arginine was introduced, with 20% piperidine/DMF, 2.5 eq of Fmoc-Cys (MBzl)-OH based on the DMBHA resin was added, and condensation reaction was carried out in DMF by the method of DIPCDI-HOBt. The degree of progress of the condensation reaction was pursued similarly to (2) by measurement according to the ninhydrin test.

(4) Introduction of amino acids of the 15- to 1-positions

Likewise as above, Lys(Boc), Arg(Mtr), Tyr(t-Bu), Cys(MBzl), Ile, Gly, Arg(Mtr), Tyr(t-Bu), Cys(MBzl), Lys-(Boc), Arg(Mtr), Tyr(t-Bu), Cys(MBzl), Trp and Arg(Mtr) residues according to as the sequence from the C-terminal amino acid were successively introduced into the DMBHA resin to obtain a protecting group-protected peptide (A) resin.

Each amino acid condensation reaction in the solid phase synthesis was carried out according to the operation conditions of the following table.

TABLE 1

| Operation | Reagent | Solvent | Time × Repeat number |
|---|---|---|---|
| Removal of Fmoc group | 20% piperidine/DMF | DMF | 5 minutes × 3 |
| Washing | — | DMF | 1 minute × 6 |
| Condensation reaction | Fmoc amino acid (2.5 eq) + DIPCDI + HOBt | DMF | 2 hours × 1 |
| Washing | — | DMF | 1 minute × 4 |

(5) Preparation of the peptide (A) by the removal of the protecting groups and operation for the removal of the resin and partial purification The protecting group-protected peptide (A) resin prepared by the operations (1) to (4) was subjected to 20% piperidine/DMF treatment to remove the Fmoc group, and then subjected to reaction at 25° C. for 2 hours in a 1 M TMSOTf-thioanisole/TFA system (10 ml of trifluoroacetic acid in the presence of m-cresol (100 eq) and ethanedthiol (300 eq)) per 100 mg of the resin. The resin was filtered off from the reaction mixture and washed twice with 1 ml of trifluoroacetic acid, 100 ml of ice-cooled dry ether was added to the mixture of the filtrate and the washing, the formed precipitate was centrifuged, and the residue was separated from the supernatant by decantation. The resulting residue was washed with cold ether, dissolved in 10 ml of 4 N AcOH, 830 mg, 80 eq of dithiothreitol was added and the mixture was stirred at room temperature overnight.

The reaction solution was centrifuged, the supernatant was treated with Sephadex G-10 (3.7×50 cm), gel filtered with 4N AcOH, and the fraction which passed through the Sephadex without stopping was collected as the main eluate part and lyophilized to obtain as powder a partially purified non-cyclized polypeptide (A).

(6) Preparation of the polypeptide (A) by air oxidation

On the other hand, a half amount of the fraction which passed through the Sephadex without stopping in the gel filtration was adjusted to pH 7.5 with concentrated aqueous ammonia, and subjected to air oxidation by aeration to carry out cyclization reaction. After the completion of air oxidation, the cyclized peptide (A) was adsorped on 10 g of Diaion HP-20 resin, and desorped and eluted with 60% CH₃CN (in 1 N AcOH), and the eluate was concentrated at room temperature under reduced pressure to remove CH₃CN and then lyophilized to give powder. The powder was dissolved in a small amount of water, and the solution was poured on an Asahipak and purified by high performance liquid chromatography (HPLC-Model 600 produced by Waters Co.) using gradient elution with CH₃CN to obtain the peptide (A) of a single peak in a yield of 27% (a value calculated based on the protecting group-protected peptide (A) resin).

(7) Analysis of the polypeptide

The amino acid composition value with leucine aminopeptidase digestion of the polypeptide purified in the above (6) accorded well with the calculated value of the composition based on the amino acid sequence of the formula (A).

Further, in the molecular weight value by FAB-MS, the calculated value of (M+H⁺) was 2309.786 and on the other hand the found value was 2310.048.

The specific rotation $[\alpha]^{20}_D$ of the obtained polypeptide was +14.2° (C=0.3, 1 N acetic acid).

EXAMPLE 2 AND COMPARATIVE EXAMPLES 1 AND 2

Antiviral activity against human immunodeficiency virus (HIV)

The antiviral activity against HIV of the polypeptide (A) synthesized in Example 1 was tested and evaluated according to the following method.

HIV-infected MT-4 cells (2.5×10⁴ cells/well, multiplicity of infection (MOI): 0.001) immediately after the infection are added together with a test substance with various changes of the concentration to a 96-well microtiter plate. After incubation at 7° C. for 5 days in a $CO_2$ incubator, the number of survivor cells is measured by the MTT method [Pauwels et al.; J. Virol. Methods, 20, 309–321 (1988)]. The antiviral activity is expressed as a concentration at which cellular affection due to HIV infection is 50% inhibited (EC 50: 50% effective concentration). On the other hand, in order to know the cytotoxicity of the test substance on the MT-4 cells, virus-non-infected cells are incubated, likewise as above, together with the test compound with various changes of the concentration. The cytotoxicity is expressed as 50% cytotoxic concentration (CC 50) due to the test substance. Further, the rough ratio of CC 50 to EC 50 (CC 50/EC 50) is expressed as an effective ratio (SI).

Table 2 shows the EC 50, CC 50 and SI values of the polypeptide (A) and, takiplesine I, a known polypeptide having an affinity to endotoxins, and azidothymidine, an anti-HIV agent, both used for comparison.

TABLE 2

| | Test drug | CC 50 (μg/ml) | EC 50 (μg/ml) | SI |
|---|---|---|---|---|
| Example 1 | Polypeptide (A) | 39 | 0.35 | 110 |
| Comparative example 1 | Tachyplesin I | 49 | 18.1 | 3 |
| Comparative exaple 2 | Azidothymidine (AZT) | 0.80 | 0.00048 | 1700 |

As apparent from the above table, the polypeptide (A) of the invention has a somewhat stronger cytotoxicity than that of Tachyplesin I whose anti-HIV activity was previously revealed, but exhibited an antiviral activity at a concentration of ⅕₀. In comparison with azidothymidine, the polypeptide (A) has an EC 50 value of higher concentration, but has a 60 times higher CC 50, indicating low cytotoxicity.

EXAMPLE 3

Table 3 shows the structural formulae and physical properties of various polypeptides [(1), (SEQ ID NO: 2); (A), (SEQ ID NO: 3); (3), (SEQ ID NO: 4); (7), (SEQ ID NO: 8); (8), (SEQ ID NO: 9); (12), (SEQ ID NO: 13); (13), (SEQ ID NO: 14); (16), (SEQ ID NO: 17): (18), (SEQ ID NO: 19); (3H), (SEQ ID NO: 4)] of the invention prepared in the same manner as in Example 1 and their antiviral activities against HIV tested and evaluated likewise in Example 2.

In the compounds of the present example in the above table, the Cys residues at the 3-, 7-, 12- and 16-positions are linked through disulfide linkage between the 3- and 16-positions and between the 7- and 12-positions, unless otherwise noted.

Further, in the above table, "AZT" denotes azidothymidine (common name: zidovudine).

Industrial Applicability

According to this invention, there can be provided a novel polypeptide or salt thereof having an antiviral activity against human immunodeficiency virus (HIV), and an anti-HIV agent containing the same as an effective ingredient.

TABLE 3

| Symbol | Compound | Physical property $[\alpha]_D^{20-22}$ | Anti-HIV activity $CC_{50}$ | $EC_{50}$ | SI |
|---|---|---|---|---|---|
| (1) | (SEQ. ID NO:2)   1 2 3 4 5 6 7 8 9 10 11 12 13 14 15 16 17 18<br>Trp-Cys-Tyr-Arg-Lys-Cys-Tyr-Arg-Gly-Ile-Cys-Tyr-Arg-Lys-Cys-Arg-NH₂ | | 207 | 6.9 | 30 |
| (A) | (SEQ. ID NO:3) Arg-Trp-Cys-Tyr-Arg-Lys-Cys-Tyr-Arg-Gly-Ile-Cys-Tyr-Arg-Lys-Cys-Arg-NH₂ | +14.2°<br>(C = 0.3 1N AcOH) | 44.6 | 0.039 | 1144 |
| (3) | (SEQ. ID NO:4) Arg-Arg-Trp-Cys-Tyr-Arg-Lys-Cys-Tyr-Arg-Gly-Ile-Cys-Tyr-Arg-Lys-Cys-Arg-NH₂ | −9.0°<br>(C = 0.1 1N AcOH) | 49.5 | 0.009 | 5500 |
| (7) | (SEQ. ID NO:8) Arg-Trp-Cys-Tyr-Arg-Lys-Cys-Tyr-Arg-Gly-Ile-Cys-Tyr-Arg-Lys-Cys-Arg-NH₂ | +10.8°<br>(C = 0.1 1N AcOH) | 46.0 | 0.13 | 354 |
| (8) | (SEQ. ID NO:9) Arg-Arg-Trp-Cys-Tyr-Arg-Lys-Cys-Tyr-Arg-Gly-Ile-Cys-Tyr-Arg-Lys-Cys-Arg-NH₂ | | 43.4 | 0.0023 | 18870 |
| (12) | (SEQ. ID NO:13) Arg-Trp-Cys-Tyr-Arg-Lys-Cys-Tyr-Arg-Gly-Ile-Cys-Tyr-Arg-Lys-Cys-Arg-NH₂ | +3.8°<br>(C = 0.1 1N AcOH) | 50.7 | 0.39 | 130 |
| (13) | (SEQ. ID NO:14) Arg-Arg-Trp-Cys-Tyr-Arg-Lys-Cys-Tyr-Arg-Gly-Ile-Cys-Tyr-Arg-Lys-Cys-Arg-NH₂ | | 48.0 | 0.007 | 6860 |
| (16) | (SEQ. ID NO:17) Arg-Trp-Cys-Trp-Arg-Lys-Cys-Trp-Lys-Gly-Leu-Cys-Tyr-Arg-Lys-Cys-Arg-NH₂ | +25.8° | 46.6 | 0.18 | 259 |

TABLE 3-continued

| Symbol | Compound | Physical property $[\alpha]_D^{20-22}$ | Anti-HIV activity | | |
|---|---|---|---|---|---|
| | | | $CC_{50}$ | $EC_{50}$ | SI |
| (18) | (SEQ. ID NO:19) Arg-Trp-Cys-Phe-Lys-Lys-Cys-Phe-Lys-Gly-Ser-Cys-Phe-Lys-Lys-Cys-Arg-NH$_2$ | (C = 0.2 1N AcOH) +5.4° (C = 0.06 1N AcOH) | 43.0 | 0.36 | 119 |
| (3H) Comparative example | (SEQ. ID NO:4) Arg-Arg-Trp-Cys-Tyr-Arg-Lys-Cys-Tyr-Arg-Gly-Ile-Cys-Tyr-Arg-Lys-Cys-Arg-NH$_2$ AZT | | 52.0 6.8 | 0.01 0.00048 | 5200 14200 |

(3H) is a reduced form of (3)

---

We claim:

1. A polypeptide, having a C-terminus, represented by formula I:

$$\begin{array}{cccccccccccc}1&2&3&4&5&6&7&8&9&10&11\\A_1-&Trp-&Cys-&A_2-&A_3-&Lys-&A_4-&A_2-&A_3-&Gly-&A_4-\end{array}$$ (I)

$$\begin{array}{cccccc}12&13&14&15&16&17\\A_4-&A_2-&A_3-&A_3-&Cys-&Arg\end{array}$$

wherein:

$A_1$ denotes a hydrogen atom or one or two amino acid residues of amino acids selected from lysine and arginine, $A_2$ independently denotes a tyrosine, phenylalanine or tryptophan residue, $A_3$ independently denotes an arginine or lysine residue, $A_4$ independently denotes an alanine, valine, leucine, isoleucine, serine, cysteine or methionine residue, Cys denotes a cysteine residue, Gly denotes a glycine residue, Lys denotes a lysine residue, Arg denotes an arginine residue, and Trp denotes a tryptophan residue; and wherein the C-terminus of the polypeptide is a carboxylic acid, or an amide or a salt thereof.

2. The polypeptide of claim 1 wherein the cysteine residues that are numbered 3 and 16 in formula I together form a cysteine.

3. The polypeptide of claim 2 wherein the cysteine residues that are numbered 7 and 12 in formula I together form a cysteine.

4. The polypeptide of claim 1 wherein $A_1$ is arginylarginine.

5. The polypeptide of claim 4 wherein the C-terminus is an amide.

6. The polypeptide of claim 4 having the following sequence:

Arg-Arg-Trp-Cys-Tyr-Arg-Lys-Cys-Tyr-Lys-Gly-Ile-Cys-Tyr-Arg-Lys-Cys-Arg (SEQ ID NO:9).

7. The polypeptide of claim 4 with the following sequence:

Arg-Arg-Trp-Cys-Tyr-Arg-Lys-Cys-Tyr-Arg-Gly-Ile-Cys-Tyr-Arg-Arg-Cys-Arg (SEQ ID NO: 14).

8. The polypeptide of claim 4 with the following sequence:

Arg-Arg-Trp-Cys-Tyr-Arg-Lys-Cys-Tyr-Arg-Gly-Ile-Cys-Tyr-Arg-Lys-Cys-Arg (SEQ ID NO:4).

9. The polypeptide of claim 5 having the following sequence:

Arg-Arg-Trp-Cys-Tyr-Arg-Lys-Cys-Tyr-Lys-Gly-Ile-Cys-Tyr-Arg-Lys-Cys-Arg (SEQ ID NO:9).

10. The polypeptide of claim 5 with the following sequence:

Arg-Arg-Trp-Cys-Tyr-Arg-Lys-Cys-Tyr-Arg-Gly-Ile-Cys-Tyr-Arg-Arg-Cys-Arg (SEQ ID NO: 14).

11. The polypeptide of claim 5 with the following sequence:

Arg-Arg-Trp-Cys-Tyr-Arg-Lys-Cys-Tyr-Arg-Gly-Ile-Cys-Tyr-Arg-Lys-Cys-Arg (SEQ ID NO: 4).

12. The polypeptide of claim 1 wherein all cysteines are in reduced form.

13. The polypeptide of claim 4 wherein all cysteines are in reduced form.

14. The polypeptide of claim 5 wherein all cysteines are in reduced form.

15. A pharmaceutical composition comprising a pharmaceutically acceptable salt of a polypeptide of claim 1.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Peptide
        ( B ) LOCATION: 1
        ( D ) OTHER INFORMATION: /label=X
            / note="X =Lys and/or Arg or hydrogen"

( i x ) FEATURE:
        ( A ) NAME/KEY: Peptide
        ( B ) LOCATION: 4
        ( D ) OTHER INFORMATION: /label=X
            / note="X =Tyr, Phe , Ala, or Trp"

( i x ) FEATURE:
        ( A ) NAME/KEY: Protein
        ( B ) LOCATION: 5
        ( D ) OTHER INFORMATION: /label=X
            / note="X =Arg or Lys"

( i x ) FEATURE:
        ( A ) NAME/KEY: Protein
        ( B ) LOCATION: 7
        ( D ) OTHER INFORMATION: /label=X
            / note="X =Ala, Val, Leu, Ile, Ser, Cys, Met"

( i x ) FEATURE:
        ( A ) NAME/KEY: Protein
        ( B ) LOCATION: 8
        ( D ) OTHER INFORMATION: /label=X
            / note="X =Tyr, Phe, Ala, or Trp"

( i x ) FEATURE:
        ( A ) NAME/KEY: Protein
        ( B ) LOCATION: 9
        ( D ) OTHER INFORMATION: /label=X
            / note="X =Arg or Lys"

( i x ) FEATURE:
        ( A ) NAME/KEY: Protein
        ( B ) LOCATION: 11

( D ) OTHER INFORMATION: /label=X
                        / note="X =Ala, Val, Leu, Ile, Ser, Cys, or Met"

( i x ) FEATURE:
                    ( A ) NAME/KEY: Protein
                    ( B ) LOCATION: 12
                    ( D ) OTHER INFORMATION: /label=X
                        / note="X =Ala, Val, Leu, Ile, Ser, Cys, or Met"

( i x ) FEATURE:
                    ( A ) NAME/KEY: Protein
                    ( B ) LOCATION: 13
                    ( D ) OTHER INFORMATION: /label=X
                        / note="X =Tyr, Phe, or Trp"

( i x ) FEATURE:
                    ( A ) NAME/KEY: Protein
                    ( B ) LOCATION: 14
                    ( D ) OTHER INFORMATION: /label=X
                        / note="X =Arg or Lys"

( i x ) FEATURE:
                    ( A ) NAME/KEY: Protein
                    ( B ) LOCATION: 15
                    ( D ) OTHER INFORMATION: /label=X
                        / note="X =Arg or Lys"

( i x ) FEATURE:
                    ( A ) NAME/KEY: Protein
                    ( B ) LOCATION: 18
                    ( D ) OTHER INFORMATION: /label=X
                        / note="X =OH or NH2"

( x i ) SEQUENCE DESCRIPTION: SEQ ID NO:1:

Xaa  Trp  Cys  Xaa  Xaa  Lys  Xaa  Xaa  Xaa  Gly  Xaa  Xaa  Xaa  Xaa  Xaa  Cys
                        1                   5                            1 0

Arg  Xaa ( 2 ) INFORMATION FOR SEQ ID NO:2:

( i ) SEQUENCE CHARACTERISTICS:
                    ( A ) LENGTH: 16 amino acids
                    ( B ) TYPE: amino acid
                    ( C ) STRANDEDNESS: single
                    ( D ) TOPOLOGY: unknown ( i i ) MOLECULE TYPE: peptide ( x i ) SEQUENCE DESCRIPTION: SEQ ID NO:2:

Trp  Cys  Tyr  Arg  Lys  Cys  Tyr  Arg  Gly  Ile  Cys  Tyr  Arg  Lys  Cys  Arg
    1                   5                            1 0                        1 5

( 2 ) INFORMATION FOR SEQ ID NO:3:

( i ) SEQUENCE CHARACTERISTICS:
                    ( A ) LENGTH: 17 amino acids
                    ( B ) TYPE: amino acid
                    ( C ) STRANDEDNESS: single
                    ( D ) TOPOLOGY: unknown ( i i ) MOLECULE TYPE: peptide ( x i ) SEQUENCE DESCRIPTION: SEQ ID NO:3:

Arg  Trp  Cys  Tyr  Arg  Lys  Cys  Tyr  Arg  Gly  Ile  Cys  Tyr  Arg  Lys  Cys
    1                   5                            1 0                        1 5

Arg ( 2 ) INFORMATION FOR SEQ ID NO:4:

( i ) SEQUENCE CHARACTERISTICS:
                    ( A ) LENGTH: 18 amino acids
                    ( B ) TYPE: amino acid ( C ) STRANDEDNESS: single
( D ) TOPOLOGY: unknown ( i i ) MOLECULE TYPE: peptide ( x i ) SEQUENCE DESCRIPTION: SEQ ID NO:4:

Arg Arg Trp Cys Tyr Arg Lys Cys Tyr Arg Gly Ile Cys Tyr Arg Lys
1               5                   10                  15
Cys Arg ( 2 ) INFORMATION FOR SEQ ID NO:5:

( i ) SEQUENCE CHARACTERISTICS:
( A ) LENGTH: 17 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:5:

Arg Trp Cys Tyr Arg Lys Cys Tyr Arg Gly Met Cys Tyr Arg Lys Cys
1               5                   10                  15
Arg ( 2 ) INFORMATION FOR SEQ ID NO:6:

( i ) SEQUENCE CHARACTERISTICS:
( A ) LENGTH: 18 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:6:

Arg Arg Trp Cys Tyr Arg Lys Cys Tyr Arg Gly Leu Cys Tyr Arg Lys
1               5                   10                  15
Cys Arg ( 2 ) INFORMATION FOR SEQ ID NO:7:

( i ) SEQUENCE CHARACTERISTICS:
( A ) LENGTH: 16 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:7:

Trp Cys Tyr Arg Lys Cys Tyr Lys Gly Ile Cys Tyr Arg Lys Cys Arg
1               5                   10                  15

( 2 ) INFORMATION FOR SEQ ID NO:8:

( i ) SEQUENCE CHARACTERISTICS:
( A ) LENGTH: 17 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:8:

Arg Trp Cys Tyr Arg Lys Cys Tyr Lys Gly Ile Cys Tyr Arg Lys Cys
1               5                   10                  15

Arg (2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:9:

```
Arg Arg Trp Cys Tyr Arg Lys Cys Tyr Lys Gly Ile Cys Tyr Arg Lys
 1               5                  10                  15
Cys Arg
```

(2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:10:

```
Arg Trp Cys Tyr Arg Lys Cys Tyr Lys Gly Leu Cys Tyr Arg Lys Cys
 1               5                  10                  15
Arg
```

(2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:11:

```
Arg Arg Trp Cys Tyr Arg Lys Cys Tyr Lys Gly Val Cys Tyr Arg Lys
 1               5                  10                  15
Cys Arg
```

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:12:

```
Trp Cys Tyr Arg Lys Cys Tyr Arg Gly Ile Cys Tyr Arg Arg Cys Arg
 1               5                  10                  15
```

(2) INFORMATION FOR SEQ ID NO:13:

(i) SEQUENCE CHARACTERISTICS:
        (A) LENGTH: 17 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:13:

```
Arg Trp Cys Tyr Arg Lys Cys Tyr Arg Gly Ile Cys Tyr Arg Arg Cys
1               5                   10                  15
Arg
```

(2) INFORMATION FOR SEQ ID NO:14:

(i) SEQUENCE CHARACTERISTICS:
        (A) LENGTH: 18 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:14:

```
Arg Arg Trp Cys Tyr Arg Lys Cys Tyr Arg Gly Ile Cys Tyr Arg Arg
1               5                   10                  15
Cys Arg
```

(2) INFORMATION FOR SEQ ID NO:15:

(i) SEQUENCE CHARACTERISTICS:
        (A) LENGTH: 17 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:15:

```
Arg Trp Cys Tyr Arg Lys Cys Tyr Arg Gly Ser Cys Tyr Arg Arg Cys
1               5                   10                  15
Arg
```

(2) INFORMATION FOR SEQ ID NO:16:

(i) SEQUENCE CHARACTERISTICS:
        (A) LENGTH: 18 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:16:

```
Arg Arg Trp Cys Tyr Arg Lys Cys Tyr Arg Gly Ala Cys Tyr Arg Arg
1               5                   10                  15
Cys Arg
```

(2) INFORMATION FOR SEQ ID NO:17:

(i) SEQUENCE CHARACTERISTICS:
        (A) LENGTH: 17 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:17:

```
Arg Trp Cys Trp Arg Lys Cys Trp Lys Gly Leu Cys Tyr Arg Lys Cys
1               5                   10                  15
```

Arg ( 2 ) INFORMATION FOR SEQ ID NO:18:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:18:

```
Arg Arg Trp Cys Trp Arg Lys Cys Trp Lys Gly Leu Cys Tyr Arg Lys
1               5                   10                  15
Cys Arg
```

( 2 ) INFORMATION FOR SEQ ID NO:19:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:19:

```
Arg Trp Cys Phe Lys Lys Cys Phe Lys Gly Ser Cys Phe Lys Lys Cys
1               5                   10                  15
Arg
```

( 2 ) INFORMATION FOR SEQ ID NO:20:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:20:

```
Arg Arg Trp Cys Phe Lys Lys Cys Phe Lys Gly Ser Cys Tyr Lys Lys
1               5                   10                  15
Cys Arg
```

( 2 ) INFORMATION FOR SEQ ID NO:21:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:21:

```
Arg Trp Cys Tyr Arg Lys Ala Tyr Lys Gly Leu Ala Tyr Arg Lys Cys
1               5                   10                  15
Arg
```

( 2 ) INFORMATION FOR SEQ ID NO:22:

( i ) SEQUENCE CHARACTERISTICS:
        ( A ) LENGTH: 18 amino acids
        ( B ) TYPE: amino acid (C) STRANDEDNESS: single
(D) TOPOLOGY: unknown (ii) MOLECULE TYPE: peptide (xi) SEQUENCE DESCRIPTION: SEQ ID NO:22:

```
Arg Arg Trp Cys Tyr Arg Lys Ala Tyr Lys Gly Val Cys Tyr Arg Lys
1               5                   10                  15
Cys Arg
```

(2) INFORMATION FOR SEQ ID NO:23:

(i) SEQUENCE CHARACTERISTICS:
(A) LENGTH: 18 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:23:

```
Arg Arg Trp Cys Tyr Arg Lys Cys Tyr Lys Gly Ile Ser Tyr Arg Lys
1               5                   10                  15
Cys Arg
```